US009827200B2

(12) United States Patent
Sekiguchi et al.

(10) Patent No.: US 9,827,200 B2
(45) Date of Patent: Nov. 28, 2017

(54) ORALLY DISINTEGRATING TABLET AND PRODUCTION PROCESS THEREFOR

(71) Applicant: Daiichi Sanyko Company, Limited, Chuo-ku, Tokyo (JP)

(72) Inventors: Gaku Sekiguchi, Hiratsuka (JP); Ryoichi Hayakawa, Yokohama (JP); Yoshihiro Hara, Hiratsuka (JP)

(73) Assignee: Daiichi Sankyo Company, Limited, Chuo-ku, Tokyo ( * ) Notice: Subject to any disclaimer, the term of this patent is extended or adjusted under 35 U.S.C. 154(b) by 427 days.

(21) Appl. No.: 14/395,428

(22) PCT Filed: Apr. 23, 2013

(86) PCT No.: PCT/JP2013/061936
§ 371 (c)(1),
(2) Date: Oct. 17, 2014

(87) PCT Pub. No.: WO2013/161823
PCT Pub. Date: Oct. 31, 2013

(65) Prior Publication Data
US 2015/0110880 A1 Apr. 23, 2015

(30) Foreign Application Priority Data
Apr. 24, 2012 (JP) ................... 2012-098770

(51) Int. Cl.
*A61K 9/20* (2006.01)
*A61K 9/00* (2006.01)
*A61K 31/13* (2006.01)
*A61K 9/50* (2006.01)

(52) U.S. Cl.
CPC .......... *A61K 9/2059* (2013.01); *A61K 9/0056* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/5026* (2013.01); *A61K 31/13* (2013.01)

(58) Field of Classification Search
None
See application file for complete search history.

(56) References Cited

U.S. PATENT DOCUMENTS

| | | | | |
|---|---|---|---|---|
| 2006/0280789 A1* | 12/2006 | Ueki | ............ | A61K 9/1635 424/464 |
| 2009/0311321 A1 | 12/2009 | Mimura | | |
| 2011/0053942 A1 | 3/2011 | Fujiwara | | |
| 2012/0082723 A1* | 4/2012 | Kudou | ............ | A61K 9/284 424/479 |

FOREIGN PATENT DOCUMENTS

| | | |
|---|---|---|
| EP | 2 050 448 A1 | 4/2009 |
| JP | 2006527774 A | 12/2006 |
| JP | 2011037840 A | 2/2011 |
| WO | 2004/112768 A1 | 12/2004 |
| WO | 2008/018371 A1 | 2/2008 |
| WO | 2009/102038 A1 | 8/2009 |

OTHER PUBLICATIONS

Mimura, K., et al., "Formulation Study for Orally Disintegrating Table Using Partly Pregelatinized Starch Binder," Chemical & Pharmaceutical Bulletin 59(8):959-964, Aug. 2011.
Notice of Reasons for Rejection dated Aug. 4, 2016, issued in corresponding Japanese Application No. 2014-512615, filed Apr. 23, 2013, 10 pages.
International Preliminary Report on Patentability dated Oct. 28, 2014, issued in corresponding International Application No. PCT/JP2013/061936, filed Apr. 23, 2013, 10 pages.
International Search Report and Written Opinion dated May 21, 2013, issued in corresponding International Application No. PCT/JP2013/061936, filed Apr. 23, 2013, 12 pages.
Obae, K., "Development of High Compactible Microcrystalline Cellulose Ceolus KG," Pharm Tech Japan 28(5):1027-1031, 2012 (This article is a summary of the Best Technology Award Lecture given in "The 28th Symposium on Particulate Design and Preparations," Oct. 28, 2011, in Osaka, Japan).
Dumarey, M., et al., "Combining Experimental Design and Orthogonal Projections to Latent Structures to Study the Influence of Microcrystalline Cellulose Properties on Roll Compaction," International Journal of Pharmaceutics 416(1):110-119, Sep. 2011.
Notification for the Opinion of Examination dated Aug. 26, 2016, issued in Taiwanese Application No. 1021114513, filed Apr. 24, 2013, 10 pages.
"Ceolus KG Is a Super-Compactibility MCC Powder. Rodform Particles. Facilitates High-Dose Formulation, Low-Compactibility Drug Tableting and Tablet Size Reduction," Asahi Kasei Chemicals Corporation, Proceedings of the Second Asian Symposium on Pharmaceutical Sciences and Technology, Xi'an, China, Sep. 19-20, 2011, p. 40.

(Continued)

*Primary Examiner* — Robert A Wax
*Assistant Examiner* — Randeep Singh
(74) *Attorney, Agent, or Firm* — Christensen O'Connor Johnson Kindness PLLC

(57) ABSTRACT

Provided are an orally disintegrating tablet that quickly disintegrates when it is placed in the mouth or put into water, provides favorable taste, has a sufficient hardness in general production, transportation and use and is excellent in terms of storage stability, and a process for the production of the same which is excellent in terms of industrial production. An orally disintegrating tablet containing a drug, a crystalline cellulose having a bulk density of 0.23 g/cm³ or less (preferably from 0.10 g/cm³ to 0.23 g/cm³), a sugar alcohol and a pregelatinized starch.

24 Claims, No Drawings

(56) References Cited

OTHER PUBLICATIONS

Chinese First Office Action, dated Jul. 29, 2015, issued in corresponding Chinese Application No. 2013800216921, filed Apr. 23, 2013, 13 pages.

* cited by examiner

ORALLY DISINTEGRATING TABLET AND PRODUCTION PROCESS THEREFOR

TECHNICAL FIELD

The present invention relates to an orally disintegrating tablet that quickly disintegrates when it is placed in the mouth or put into water and has sufficient hardness in general production, transportation and use, and a process for the production of the same.

BACKGROUND ART

As dosage forms for oral solid formulations in the field of medicaments and foods, tablets, capsules, granules, powders and the like are known, and development of an orally disintegrating tablet that quickly disintegrates when it is placed in the mouth or put into water, as a dosage form that is taken more easily by the elderly, children and aphagia patients, is desired.

An orally disintegrating tablet is required to have the property of disintegrating quickly in the oral cavity, and to have a sufficient hardness that, like conventional tablets, it may tolerate physical impacts in production, transportation and use.

Furthermore, it is desirable in view of drug compliance that unpleasant taste and irritation are suppressed and favorable taste is provided when the tablet is placed in the mouth.

Various orally disintegrating tablets have been reported. For example, Patent Literature 1 describes an orally disintegrating tablet comprising: a) mitiglinide calcium hydrate, which is a drug having a bitter taste, b) a crystalline cellulose, and c) a granulated product comprising at least one kind selected from aminoalkyl methacrylate copolymer E and the like as a masking agent, d) a sugar or sugar alcohol, and e) at least one kind selected from corn starch and a partially-pregelatinized starch. This literature explains that the crystalline cellulose is incorporated in a granulated drug product and has the effect of enhancing the dissolution properties of the drug, and does not describe the effect of the kind of the crystalline cellulose on the oral disintegration properties and tablet hardness. Furthermore, this literature describes that, in the case where a sugar alcohol that is difficult to compression-mold directly with the drug-containing granulated product is used, it is desirable that the sugar alcohol be used after granulating it in advance, and further describes that, in the case where D-mannitol is used as the sugar alcohol, a partially-pregelatinized starch is preferable as a binder, and that a partially-pregelatinized starch comprising a cold water-soluble component of about 10 to 20% by weight is preferable so as to suppress generation of tabletting failure and to impart a suitable tablet hardness and the property of quick oral disintegration. However, in this literature, D-mannitol is always granulated with corn starch which is added in the granulating process.

Patent Literature 2 describes an orally disintegrating tablet comprising granulated drug granules obtainable by wet-granulation by adding an aqueous solution comprising a monosaccharide to a powder comprising a drug, and also describes that it is preferable to incorporate a crystalline cellulose and corn starch, which are hardly-soluble components, and specifically describes that the crystalline cellulose is preferably used since it has a property by which the friability of the tablet can be improved by incorporation of a small amount of the crystalline cellulose. This literature describes that it is essential that the drug-containing powder be wet-granulated with an aqueous solution comprising a water-soluble monosaccharide, and excellent forming properties and disintegration properties as an orally disintegrating tablet can be obtained by doing so.

Patent Literature 3 describes an orally disintegrating tablet comprising (1) an active ingredient, (2) mannitol, (3) a crystalline cellulose and (4) at least two specific components selected from the group consisting of low-substituted hydroxypropyl cellulose, corn starch and carmellose, wherein the incorporation amounts of the respective components are 0.01 to 50% by weight for (1), 20 to 86% by weight for (2), 10 to 30% by weight for (3), and the incorporation amounts of each of the respective specific components (4) is 1 to 20% by weight, and the total of the specific components as incorporated is 3 to 60% by weight, with respect to 100% by weight of the disintegrating tablet, and the incorporated crystalline cellulose (3), in the form of an aggregate, has a bulk density of 0.18 $g/cm^3$ or less. This literature explains that the desired effect of the orally disintegrating tablet described in this literature is achieved by the combination of the crystalline cellulose having a specific bulk density (3) and the at least two kinds of specific components selected from the group consisting of the low-substituted hydroxypropyl cellulose, corn starch and carmellose (4), and the desired effect cannot be obtained if either of these is absent.

CITATION LIST

Patent Literatures

Patent Literature 1: International Publication WO2008/018371

Patent Literature 2: Japanese Patent Application Laid-Open No. 2011-37840

Patent Literature 3: International Publication WO 2009/102038

SUMMARY OF INVENTION

Technical Problem

The object of the present invention is to provide an orally disintegrating tablet that quickly disintegrates when it is placed in the mouth or put into water, provides favorable taste, has a sufficient hardness in general production, transportation and use, and is excellent in terms of storage stability.

Another object of the present invention is to provide a method for producing an orally disintegrating tablet having the above-mentioned excellent properties by conventional compression without requiring special equipment, which is excellent in terms of industrial production.

Solution to Problem

The present inventors have undertaken intensive studies aimed at solving the above-mentioned problem, and consequently found that the above-mentioned problem is solved by incorporating a crystalline cellulose having a bulk density of 0.23 $g/cm^3$ or less, a sugar alcohol and a pregelatinized starch in combination, and thereby completed the present invention.

Specifically, the present invention provides an orally disintegrating tablet comprising a drug, a crystalline cellulose having a bulk density of 0.23 $g/cm^3$ or less, a sugar alcohol and a pregelatinized starch, and a method for producing the same.

Specifically, the present invention relates to the following (1) to (33).

(1) An orally disintegrating tablet comprising a drug, a crystalline cellulose having a bulk density of 0.23 g/cm$^3$ or less, a sugar alcohol and a pregelatinized starch.

(2) The orally disintegrating tablet according to (1), wherein the crystalline cellulose has a bulk density of from 0.10 g/cm$^3$ to 0.23 g/cm$^3$.

(3) The orally disintegrating tablet according to (1) or (2), wherein the crystalline cellulose has a bulk density of 0.15 g/cm$^3$ or less.

(4) The orally disintegrating tablet according to any one of (1) to (3), wherein the incorporation amount of the crystalline cellulose in the disintegrating tablet is 5 to 50% by weight.

(5) The orally disintegrating tablet according to any one of (1) to (4), wherein the pregelatinized starch has an average degree of gelatinization of 90% or less (preferably 70 to 80%).

(6) The orally disintegrating tablet according to any one of (1) to (5), wherein the sugar alcohol is D-mannitol.

(7) The orally disintegrating tablet according to any one of (1) to (6), further comprising a disintegrating agent.

(8) The orally disintegrating tablet according to (7), wherein the disintegrating agent is one kind or two or more kinds selected from the group consisting of crospovidone, carmellose calcium, carmellose, croscarmellose sodium, low-substituted hydroxypropyl cellulose, corn starch and sodium starch glycolate.

(9) The orally disintegrating tablet according to any one of (1) to (8), further comprising a lubricant.

(10) The orally disintegrating tablet according to (9), wherein the lubricant is one kind or two or more kinds selected from the group consisting of magnesium stearate, calcium stearate, sodium stearyl fumarate and talc.

(11) The orally disintegrating tablet according to any one of (1) to (10), wherein the drug is memantine or a pharmaceutically acceptable salt thereof.

(12) The orally disintegrating tablet according to (11), wherein the pharmaceutically acceptable salt of memantine is memantine hydrochloride.

(13) An orally disintegrating tablet obtainable by compressing drug-free granules comprising a crystalline cellulose having a bulk density of 0.23 g/cm$^3$ or less, a sugar alcohol and a pregelatinized starch, and a drug or drug-containing granules.

(14) The orally disintegrating tablet according to (13), wherein the drug-free granules are obtainable by granulating a mixed powder comprising a crystalline cellulose having a bulk density of 0.23 g/cm$^3$ or less and a sugar alcohol with a liquid in which a pregelatinized starch is dissolved or dispersed.

(15) The orally disintegrating tablet according to (13) or (14), wherein a disintegrating agent is further incorporated in the drug-containing granules or drug-free granules, or outside of the granules.

(16) The orally disintegrating tablet according to (15), wherein the disintegrating agent is one kind or two or more kinds selected from the group consisting of crospovidone, carmellose calcium, carmellose, croscarmellose sodium, low-substituted hydroxypropyl cellulose, corn starch and sodium starch glycolate.

(17) An orally disintegrating tablet obtainable by compressing a drug-free mixed powder comprising a crystalline cellulose having a bulk density of 0.23 g/cm$^3$ or less, a sugar alcohol and a pregelatinized starch, and a drug or drug-containing granules.

(18) The orally disintegrating tablet according to (17), wherein a disintegrating agent is further incorporated in the drug-containing granules or outside of the granules.

(19) The orally disintegrating tablet according to (18), wherein the disintegrating agent is one kind or two or more kinds selected from the group consisting of crospovidone, carmellose calcium, carmellose, croscarmellose sodium, low-substituted hydroxypropyl cellulose, corn starch and sodium starch glycolate.

(20) An orally disintegrating tablet obtainable by compressing drug-containing granules comprising a drug, a crystalline cellulose having a bulk density of 0.23 g/cm$^3$ or less, a sugar alcohol and a pregelatinized starch.

(21) The orally disintegrating tablet according to (20), wherein a disintegrating agent is further incorporated in the drug-containing granules or outside of the granules.

(22) The orally disintegrating tablet according to (21), wherein the disintegrating agent is one kind or two or more kinds selected from the group consisting of crospovidone, carmellose calcium, carmellose, croscarmellose sodium, low-substituted hydroxypropyl cellulose, corn starch and sodium starch glycolate.

(23) The orally disintegrating tablet according to any one of (13) to (22), wherein the drug-containing granules are a particulate substance comprising a drug having a coating formed thereon.

(24) The orally disintegrating tablet according to (23), wherein the drug is memantine or a pharmaceutically acceptable salt thereof.

(25) A process for the production of an orally disintegrating tablet, comprising mixing and compressing a granulated product, a powdery or granulated drug, and an additive where desired, wherein the granulated product is obtainable by wet-granulating a mixture comprising a crystalline cellulose having a bulk density of 0.23 g/cm$^3$ or less and a sugar alcohol with a liquid in which a pregelatinized starch is dissolved or dispersed, or by wet-granulating a mixture comprising the crystalline cellulose having a bulk density of 0.23 g/cm$^3$ or less, the sugar alcohol and the pregelatinized starch with water and drying the product.

(26) A process for the production of an orally disintegrating tablet, comprising compressing a mixture obtainable by mixing a powdery or granulated drug, a crystalline cellulose having a bulk density of 0.23 g/cm$^3$ or less, a sugar alcohol and a pregelatinized starch.

(27) A process for the production of an orally disintegrating tablet, comprising mixing and compressing a granulated product, and an additive where desired, wherein the granulated product is obtainable by wet-granulating a mixture comprising a powdery drug, a crystalline cellulose having a bulk density of 0.23 g/cm$^3$ or less and a sugar alcohol with a liquid in which a pregelatinized starch is dissolved or dispersed, or by wet-granulating a mixture comprising the powdery drug, the crystalline cellulose having a bulk density of 0.23 g/cm$^3$ or less, the sugar alcohol and the pregelatinized starch with water and drying the product.

(28) The process for the production of an orally disintegrating tablet according to (25) or (27), wherein the wet-granulation is fluidized bed granulation.

(29) The process for the production of an orally disintegrating tablet according to any one of (25) to (28), wherein a disintegrating agent is further included in the mixture or additive.

(30) The process for the production of an orally disintegrating tablet according to any one of (25) to (29), which comprises adding a lubricant before conducting the compression.

(31) The process for the production of an orally disintegrating tablet according to any one of (25) to (30), wherein the powdery or granulated drug comprises a coating provided on the surface of the drug.

(32) The process for the production of an orally disintegrating tablet according to any one of (22) to (31), wherein the drug is memantine or a pharmaceutically acceptable salt thereof.

(33) The process for the production of an orally disintegrating tablet according to (32), wherein the memantine or a pharmaceutically acceptable salt thereof is memantine hydrochloride.

Advantageous Effects of Invention

The present invention was able to provide an orally disintegrating tablet that has the property of quick disintegration and solubility when it is placed in the oral cavity or put into water, provides favorable taste, has a sufficient hardness in the processes of general production, transportation and use, and is excellent in terms of storage stability.

Furthermore, the present invention was able to provide a process for producing an orally disintegrating tablet having the above-mentioned excellent properties by conventional compression without requiring complex steps and special equipment.

DESCRIPTION OF EMBODIMENTS

In the present invention, an orally disintegrating tablet is a compressed product that has the property of quick disintegration and solubility when it is placed in the mouth or put into water. Specifically, it means a tablet that disintegrates in generally about 5 to 120 seconds, preferably about 5 to 60 seconds, further preferably about 5 to 40 seconds, typically in a disintegration test in saliva in the oral cavity, a disintegration test in an apparatus, or the like.

The drug in the present invention is not specifically limited as long as it is a component that can be administered orally, which is used for the treatment, prevention or diagnosis of a disease. The orally disintegrating tablet of the present invention is particularly suitable for a drug to be administered to the elderly, children or aphagia patients, and examples may include an antipyretic analgesic-antiinflammatory agent, a psychotropic drug, an antianxiety drug, a sedative-hypnotic agent, an antidepressant drug, a central nervous system drug, a drug for the treatment of schizophrenia, an antiepileptic drug, an anticonvulsant drug, an anti-spasm agent, an anti-Parkinson's disease therapeutic agent, a antidiabetic agent, an agent for liver disorder, a drug for the treatment of dysuria, a gastrointestinal drug, an antiulcer agent, an antacid, a brain metabolic stimulant, an antitussive-expectorant drug, an antiallergic drug, a bronchodilator drug, a cardiotonic drug, an antiarrhythmic drug, a drug for heart failure, a drug for atrial fibrillation, an antihistamine drug, a diuretic drug, a hypotensive drug, an antiarteriosclerotic drug, an organ-protective agent, a vasoconstricting drug, a choleretic drug, a hypolipidemic drug, a coronary vasodilating drug, a peripheral vasodilatating drug, an antiplasmin agent, an anticoagulant agent, an antiplatelet agent, an antibiotic, an antimicrobial agent, an anti-influenza drug, an agent for improving liver function, a drug for the treatment of gout, a drug for the treatment of Alzheimer-type dementia, a drug for the treatment of cancer pain, and the like. Examples of the antipyretic analgesic-antiinflammatory agent may include loxoprofen sodium hydrate, N-methyl-scopolamine methylsulfate, pentazocine hydrochloride, mefenamic acid, epirizole, etc. Examples of the antianxiety drug may include cloxazolam, oxazolam, timiperone, nitrazepam, and etizolam. Examples of the hypnotic drug may include haloxazolam etc. Examples of the antidepressant drug may include lofepramine hydrochloride, mianserin hydrochloride, lithium carbonate, etc. Examples of the drug for the treatment of schizophrenia may include oxypertine. Examples of the antiepileptic drug may include sodium valproate, phenytoin, carbamazepine, etc. Examples of the anticonvulsant drug may include phenobarbital, etc. Examples of the anti-spasm agent may include baclofen, etc. Examples of the anti-Parkinson's disease therapeutic agent may include levodopa, trihexyphenidyl hydrochloride, etc. Examples of the antidiabetic agent may include metformin, pioglitazone hydrochloride, teneligliptin hydrobromide, sitagliptin phosphate hydrate, vildagliptin, alogliptin benzoate, linagliptin, anagliptin, etc. Examples of the agent for liver disorder may include malotilate, diisopropylamine dichloroacetate, etc. Examples of the drug for the treatment of dysuria may include tamsulosin hydrochloride, naftopidil, etc. Examples of the antiulcer agent may include famotidine, omeprazole, lansoprazole, sodium rabeprazole, etc. Examples of the antacid may include sodium alginate, calcium carbonate, magnesium carbonate, magnesium hydroxide, etc. Examples of the brain metabolic stimulant may include gamma-aminobutyric acid, etc. Examples of the antitussive-expectorant drug may include carbocysteine, etc. Examples of the antiallergic drug may include cetirizine hydrochloride, etc. Examples of the bronchodilator drug may include theophylline, etc. Examples of the cardiotonic drug may include digoxin, etc. Examples of the antiarrhythmic drug may include procainamide hydrochloride, bepridil hydrochloride hydrate, etc. Examples of the diuretic drug may include hydrochlorothiazide, furosemide, bumetanide, etc. Examples of the drug for heart failure may include carvedilol, bisoprolol fumarate, etc. Examples of the hypotensive drug may include carvedilol, bisoprolol fumarate, metoprolol tartrate, reserpine, temocapril hydrochloride, olmesartan medoxomil, candesartan cilexetil, valsartan, telmisartan, irbesartan, losartan potassium, azilsartan, aliskiren fumarate, azelnidipine, amlodipine besilate, budralazine, etc. Examples of the vasoconstricting drug may include midodrine hydrochloride, etc. Examples of the choleretic drug may include ursodeoxycholic acid, etc. Examples of the hypolipidemic drug may include pravastatin sodium, atorvastatin calcium, rosuvastatin, etc. Examples of the coronary vasodilating drug may include dipyridamole, nicorandil, etc. Examples of the peripheral vasodilatating drug may include isoxsuprine hydrochloride, etc. Examples of the antiplasmin agent may include tranexamic acid, etc. Examples of the anticoagulant agent may include edoxaban tosilate hydrate, etc. Examples of the antiplatelet agent may include ticlopidine hydrochloride, cilostazol, etc. Examples of the antimicrobial agent may include nalidixic acid, levofloxacin hydrate, sitafloxacin hydrate, ofloxacin, etc. Examples of the anti-influenza drug may include oseltamivir, etc. Examples of the antibiotic may include cefuroxime axetil, chloramphenicol, cefpodoxime proxetil, etc. Examples of the drug for the treatment of gout may include allopurinol, febuxostat, etc. Examples of the drug for the treatment of Alzheimer-type dementia may include memantine, donepezil, etc. Examples of the drug for the treatment of cancer pain may include hydromorphone, etc.

Among these, the orally disintegrating agent of the present invention is particularly suitable for loxoprofen sodium hydrate, which is used as the antipyretic analgesic-antiinflammatory agent; carvedilol and bisoprolol fumarate, which are used as the drug for heart failure or as the hypotensive drug; olmesartan medoxomil and azilsartan, which are used as the hypotensive drug; pravastatin sodium, which is used as the hypolipidemic drug; levofloxacin hydrate and sitafloxacin hydrate, which are used as the antimicrobial agent; edoxaban tosilate hydrate, which is used as the anticoagulant agent; memantine or a pharmaceutically acceptable salt thereof (specifically memantine hydrochloride) and donepezil or a pharmaceutically acceptable salt thereof (specifically donepezil hydrochloride), which are used as drugs for the treatment of Alzheimer-type dementia; and hydromorphone, which is used as a drug for the treatment of cancer pain.

Two or more kinds of drugs may be incorporated in combination so as to exert the effect of the treatment, prevention or diagnosis of the target disease.

Furthermore, where desired, the drug may be used by coating the surface of a powdery drug (the surface of a crystal) or the granulate surface of a granulated drug. The coating is provided in order to mask unpleasant taste, odor or irritation derived from the drug to make dosing easy, to protect the drug from light, water, oxygen and the like, to improve stability by separating components that readily cause composition change, to improve the effectiveness and stability of the drug by making the drug enteric or sustained, and the like, and the coating process and the coating agent are selected according to the purpose. A process commonly-used in the field of formulation techniques can be used for the coating, and the coating is conducted by using, for example, a fluidized bed granulation-coating machine, a tumbling fluidized bed granulation-coating machine, a centrifuge fluidized bed granulation-coating machine, a Wurster-type fluidized bed granulation-coating machine or the like.

In the present invention, a crystalline cellulose having a bulk density of 0.23 g/cm$^3$ or less is used. The bulk density of the crystalline cellulose can be measured by the measurement method described in the entry for Crystalline Cellulose in the 16th Revised Japanese pharmacopeias, which was defined based on the agreement of the pharmacopeias in the three regions of Japan, Europe and the United States. The bulk density is preferably from 0.10 g/cm$^3$ to 0.23 g/cm$^3$, more preferably from 0.10 g/cm$^3$ to 0.15 g/cm$^3$.

As the crystalline cellulose having a bulk density of 0.23 g/cm$^3$ or less, a commercially available one can be used. Examples may include CEOLUS KG-1000 (bulk density: 0.10 to 0.15 g/cm$^3$) and CEOLUS KG802 (bulk density: 0.13 to 0.23 g/cm$^3$) (they are both manufactured by Asahi Kasei Chemicals Corporation). Alternatively, one obtained by combining two or more kinds of crystalline celluloses having different bulk densities so as to give a desired bulk density can also be used.

The incorporation amount of the above-mentioned crystalline cellulose is preferably from 5 to 50% by weight per 100% by weight of the orally disintegrating tablet. When the incorporation amount exceeds 50% by weight, it is possible that the flowability will deteriorate and the ease of production will decrease. A more preferable incorporation amount is 10 to 40% by weight.

The above-mentioned crystalline cellulose may be formed into a tabletting powder by mixing it with other components in its original powdery form, and compressed, or may be granulated by using a suitable binder and subjected to compression.

Examples of the sugar alcohol used in the present invention may be D-mannitol, erythritol, xylitol, maltitol, sorbitol and the like, and D-mannitol is preferable. D-mannitol that complies with the pharmacopeias in Japan, Europe and the United States can generally be used. Although the crystal form, particle diameter and specific surface area of the D-mannitol to be incorporated are not specifically limited, the crystal form may be any of Type α, Type β, Type δ and amorphous, the particle diameter is preferably from 10 μm to 250 μm, more preferably from 20 μm to 150 μm, the specific surface area is preferably from 0.1 m$^2$/g to 4 m$^2$/g, more preferably from 0.1 m$^2$/g to 2 m$^2$/g, and the crystal form, particle diameter and specific surface area can be measured by X-ray diffractometry, a laser diffraction particle size measurement method and a BET specific surface area measurement method (multipoint method), respectively. Examples of commercially available D-mannitols may include D-mannitols available from Merck Corporation, Roquette Corporation, Towa Chemical Industry Co., Ltd., Kao Corporation and the like.

The incorporation amount of the above-mentioned sugar alcohol can suitably be selected. In the case where D-mannitol is used, it is generally 20 to 95% by weight, preferably 30 to 85% by weight per 100% by weight of the orally disintegrating tablet.

The sugar alcohol may be formed into a tabletting powder by mixing it with other components in its original powdery form, and compressed, or may be granulated by using a suitable binder and subjected to compression.

The pregelatinized starch used in the present invention is gelatinized by a heat treatment of starch, and one described in the Japan Pharmaceutical Excipients can be used. The average degree of gelatinization is preferably 90% or less, more preferably 70 to 80%. As a commercially available pregelatinized starch, for example, the pregelatinized starch swelstar PD-1 (manufactured by Asahi Kasei Chemicals Corporation) can be used.

The incorporation amount of the above-mentioned pregelatinized starch is generally 1 to 15% by weight, preferably 1 to 10% by weight per 100% by weight of the orally disintegrating tablet.

The pregelatinized starch may be formed into a tabletting powder by mixing it with other components in its original powdery form, and compressed, or may be granulated together with other components and subjected to compression.

In the orally disintegrating tablet of the present invention, the pregelatinized starch plays the role of a disintegrating agent. On the other hand, the pregelatinized starch imparts viscosity when it is dissolved or dispersed in a liquid such as water. Thus, when the liquid in which the pregelatinized starch is dissolved or dispersed is sprayed onto a powdery raw material, granulation proceeds and the pregelatinized starch and the raw material are formed into granules. By utilizing this property, a tablet having favorable moldability and desired orally disintegrating properties can be obtained by:

preparing granules using a fluidized bed granulation process which includes spraying the liquid in which the pregelatinized starch is dissolved or dispersed onto a powdery mixture comprising a crystalline cellulose having a bulk density of 0.23 g/cm$^3$ or less and a sugar alcohol;

mixing the granules with other components where necessary; and compressing the mixture.

Such advantages in terms of production are particular to the pregelatinized starch, and can largely not be obtained in the case where a commonly-used disintegrating agent such as low-substituted hydroxypropyl cellulose and crospovidone is used.

The orally disintegrating tablet of the invention may further comprise a disintegrating agent in addition to the above-mentioned components. Examples of the disintegrating agent may include one kind or combinations of two or more kinds selected from crospovidone (for example, a product that is compliant with the Pharmaceutical Excipients), carmellose calcium (for example, a product that is compliant with the Japanese Pharmacopoeia), carmellose (for example, a product that is compliant with the Japanese Pharmacopoeia), croscarmellose sodium (for example, a product that is compliant with the Japanese Pharmacopoeia), low-substituted hydroxypropyl cellulose (for example, a product that is compliant with the Japanese Pharmacopoeia), corn starch (for example, a product that is compliant with the Japanese Pharmacopoeia), sodium starch glycolate (for example, a product that is compliant with the Japanese Pharmacopoeia), and crospovidone, carmellose calcium and low-substituted hydroxypropyl cellulose are specifically preferable.

The incorporation amount of the disintegrating agent is generally 0.5 to 20% by weight, preferably 1 to 10% by weight per 100% by weight of the orally disintegrating tablet.

The orally disintegrating tablet of the present invention may further comprise a lubricant. Examples of the lubricant may include one kind or combinations of two or more kinds selected from magnesium stearate (for example, a product that is compliant with the Japanese Pharmacopoeia), calcium stearate (for example, a product that is compliant with the Japanese Pharmacopoeia), sodium stearyl fumarate (for example, a product that is compliant with the Pharmaceutical Excipients) and talc (for example, a product that is compliant with the Japanese Pharmacopoeia), and magnesium stearate is specifically preferable.

The incorporation amount of the lubricant is generally 0.1 to 3.0% by weight, preferably 0.5 to 1.5% by weight per 100% by weight of the orally disintegrating tablet.

The orally disintegrating tablet of the present invention can comprise various ingredients that are generally used in the production of tablets as long as the effect of the invention is not impaired.

Examples of the additives may include an excipient, a binder, a coating agent, a plasticizer, a colorant, a flavoring agent, a sweetener, a taste-masking agent, a fluidizing agent, a foaming agent and a surfactant, and the like.

Examples of the excipient may include organic excipients selected from saccharides, sugar alcohols, starches and celluloses, and inorganic excipients. Examples of the saccharides may include one or combinations of two or more selected from lactose, sucrose, fructo-oligosaccharide, glucose, palatinose, maltose, reduced maltose, powder sugar, koui, fructose, isomerized lactose and honey Examples of the sugar alcohol may include D-mannitol, erythritol, xylitol, maltitol, sorbitol and the like. Examples of the starches may include one or combinations of two or more selected from corn starch, potato starch, rice starch, partially-pregelatinized starch and pregelatinized starch. Examples of the celluloses may include, in addition to the crystalline cellulose, one or combinations of two or more selected from powder cellulose, low-substituted hydroxypropyl cellulose, carmellose, carmellose calcium and croscarmellose sodium. Examples of the inorganic excipients may include one or combinations of two or more selected from synthesized hydrotalcite, sedimented calcium carbonate, hydrous silicon dioxide, light anhydrous silicic acid, magnesium aluminosilicate and magnesium hydroxide.

Examples of the binder may include one or combinations of two or more selected from gum arabic, sodium alginate, carboxyvinyl polymer, gelatin, dextrin, pectin, sodium polyacrylate, pullulan, methyl cellulose, hydroxypropyl cellulose, hydroxypropyl methyl cellulose, polyvinyl alcohol, polyvinyl pyrrolidone and macrogol.

As a coating agent for coating the surface of a powdery drug (the surface of a crystal) or the granulate surface of a granulated drug, one or combinations of two or more selected from ethyl cellulose, aminoalkyl methacrylate copolymer E, methacrylic acid copolymer L, dried methacrylic acid copolymer LD, methacrylic acid copolymer LD, methacrylic acid copolymer S, aminoalkyl methacrylate copolymer RS, ethyl acrylate-methyl methacrylate copolymer, polyvinyl acetal-diethylamino acetate and polyvinyl acetate resin may be included.

Examples of the plasticizer to be combined with the coating agent may include one or combinations of two or more selected from diethyl sebacate, dibutyl sebacate, triethyl citrate, stearic acid, polyethylene glycol and triacetine.

Examples of the colorant may include one or combinations of two or more selected from food colorants such as Food Yellow No. 5, Food Red No. 2 and Food Blue No. 2; food lake colorant, yellow ferric oxide, ferric oxide, titanium oxide, β-carotene and riboflavin.

Examples of the flavoring agent may include one or combinations of two or more selected from orange, lemon, strawberry, mint, menthol, Menthol Micron and various flavor materials.

Examples of the sweetener may include one or combinations of two or more selected from saccharin sodium, saccharin, Aspartame, Acesulfame potassium, dipotassium glycyrrhizate, sucralose, stevia and thaumatin.

Examples of the taste-masking agent may include one or combinations of two or more selected from sodium chloride, magnesium chloride, disodium inosinate, sodium L-glutamate and honey.

Examples of the surfactant may include one or combinations of two or more selected from Polyoxyl 40 stearate, sorbitan aliphatic acid esters, polyoxyethylene hydrogenated castor oil, Polysolbate, glycerin monostearate and sodium laurylsulfate.

Examples of the foaming agent may include tartaric acid and/or citric acid.

Examples of the fluidizing agent may include one or combinations of two or more selected from hydrous silicon dioxide, light anhydrous silicic acid and talc.

Hereinafter, embodiments A to C of the orally disintegrating tablet of the present invention will be explained together with the production processes therefor.

Embodiment A

An orally disintegrating tablet obtainable by compressing drug-free granules comprising a crystalline cellulose having a bulk density of 0.23 g/cm$^3$ or less, a sugar alcohol and a pregelatinized starch, and a drug or drug-containing granules.

In the present embodiment, the drug-free granules act as a backbone for a formulation that can impart desirable disintegration properties and moldability to an orally disintegrating tablet, irrespective of the properties inherent to the drug. Although the drug-free granules exert excellent disintegration properties and moldability by incorporating only three components—the crystalline cellulose having a bulk density of 0.23 g/cm³ or less, sugar alcohol and pregelatinized starch—other ingredients may be incorporated where necessary.

The ratio of sugar alcohol to crystalline cellulose having a bulk density of 0.23 g/cm³ or less in the drug-free granules is 1 to 10 parts by weight (sugar alcohol) to 1 parts by weight (crystalline cellulose), preferably 1.5 to 8.5 parts by weight (sugar alcohol), more preferably 1.5 to 2.5 parts by weight (sugar alcohol) in the case where D-mannitol is used as the sugar alcohol.

The drug-free granules can be produced only from components of a crystalline cellulose having a bulk density of 0.23 g/cm³ or less, a sugar alcohol such as D-mannitol and a pregelatinized starch. When this is the case, the amounts of each component are 50 to 90% by weight (preferably, 55 to 75% by weight) of sugar alcohol such as D-mannitol, 10 to 40% by weight (preferably, 20 to 35% by weight) of crystalline cellulose having a bulk density of 0.23 g/cm3 or less, and 2 to 5% by weight (preferably, 3 to 4% by weight) of pregelatinized starch.

The process for producing the orally disintegrating tablet of embodiment A comprises the steps of: Producing drug-free granules, producing drug-containing granules where desired, mixing the drug-free granules with a drug or the drug-containing granules and other ingredients, and compressing the mixture.

A-1: Step of Producing Drug-Free Granules

Drug-free granules can be manufactured by the following processes (1) and (2).

1) A process for wet-granulating a mixture comprising a crystalline cellulose having a bulk density of 0.23 g/cm³ or less, a sugar alcohol (for example, D-mannitol) and a pregelatinized starch with water.

2) A process of granulating a mixture comprising a crystalline cellulose having a bulk density of 0.23 g/cm³ or less and a sugar alcohol (for example, D-mannitol) with a liquid such as water in which a pregelatinized starch is dissolved or dispersed.

For the granulation, a commonly-used extrusion granulation process, a mixing-stirring granulation process, a high-shear granulation process, a fluidized bed granulation process, a rotary granulation process or the like can be used.

The pregelatinized starch exhibits a viscosity suitable for granulation when it is dissolved or dispersed in a liquid such as water. The present inventors produced a tablet obtained by mixing a pregelatinized starch in its original powdery form with other components and granulating the mixture to give granules and compressing the granules, and a tablet obtained by granulating from a liquid in which a pregelatinized starch is dissolved or dispersed in water to give granules and compressing the granules, and compared their disintegrating properties and hardnesses, and found that both tablets had desired properties but the latter was more excellent.

Furthermore, the present inventors also compared the disintegrating properties and hardnesses and the like between tablets obtained by compressing granules produced by a high-shear granulation process and a fluidized bed granulation process, respectively, in the case where granulation is conducted by using a liquid in which a pregelatinized starch is dissolved or dispersed, and found that both processes can be applied but a more excellent orally disintegrating tablet can be obtained in the case where the granules are produced by using the fluidized bed granulation process.

In the case where other ingredients such as a commonly-used disintegrating agent is added to the drug-free granules, it may be added to the mixture before granulation.

A-2: Step of Producing Drug-Containing Granules

The drug can be mixed with the drug-free granules in its original powdery form, or after being formed into a granular form where desired. The drug-containing granules can be produced by, for example, a commonly-used extrusion granulation process, a mixing-stirring granulation process, a high-shear granulation process, a fluidized bed granulation process, a tumbling granulation process or the like.

Alternatively, the drug-containing granules can be formed by granulating a mixed powder of a powdery or granular drug, a crystalline cellulose having a bulk density of 0.23 g/cm³ or less and a sugar alcohol with a liquid suspension of a pregelatinized starch.

The drug or drug-containing granules can be provided with a coating so as to mask unpleasant tastes such as bitter tastes and tastes with irritant properties, and odors, and to control dissolution properties. For the coating, the above-mentioned coating agent and plasticizer can suitably be used. The coating process is conducted by using, for example, a fluidized bed granulation-coating machine, a tumbling fluidized bed granulation-coating machine, a centrifuge fluidized bed granulation-coating machine or a Wurster-type fluidized bed granulation-coating machine.

Further, the drug-containing granules which are masked against unpleasant tastes or odors may be prepared as follows. A waxy substance is melted with heat, and the drug and optional components of sugar alcohol, synthetic aluminum silicate, hydrous silicon dioxide etc. are dispersed or dissolved therein. Subsequently, the resultant dispersion or solution is subjected to spray granulation.

In the case where two or more kinds of drugs are used, the drugs can be incorporated in the same granules or incorporated respectively in separate granules according to the compatibility of the drugs, and subjected to compression.

A-3: Step of Mixing Drug-Free Granules with Drug or Drug-Containing Granules and Other Ingredients, and Compression The drug-free granules are mixed with the drug or drug-containing granules, and a disintegrating agent, a lubricant and other ingredients, and the mixture is compressed to give an orally disintegrating tablet. The mixing is conducted, for example, using a tumble mixer or a convector mixer.

The orally disintegrating tablet of the present invention can be compressed using a conventional tabletting machine. Although the pressure for compressing by a tabletting machine may be approximately equal to those for conventional tablets, and depends on the form and size of the tablet, it is preferably about 2 to 20 kN, more preferably about 4 to 14 kN.

The percentage of the drug-free granules in the tablet by weight can be 30 to less than 100. In the case where the drug is powdery, the percentage of the drug-free granules is 60 to less than 100. In the case where the drug is used after granulating, the percentage of the drug-free granules is 30 to 85, preferably 35 to 80. Further, the relative amount by weight of drug-free granules to drug-containing granules is 0.5 to 5.0 parts (drug-free granules) to 1 part (drug-containing granules) in the case where the drug is used after granulating.

The average particle size of the drug-free granules is 40 to 150 μm, preferably 60 to 150 μm when it is determined according to the Japanese Pharmacopoeia 16th edition "Particle Size Determination Method 2. Analytical Sieving Method" by sieving and calculating using a logarithmic integral method.

Embodiment B

An orally disintegrating tablet obtainable by compressing a drug-free mixed powder comprising a crystalline cellulose having a bulk density of 0.23 g/cm$^3$ or less, a sugar alcohol and a pregelatinized starch, and a drug or drug-containing granules.

In this embodiment, the drug-free mixed powder imparts desirable disintegration properties and moldability to an orally disintegrating tablet. Although the drug-free mixed powder exerts excellent disintegration properties and moldability by incorporating only three components—the crystalline cellulose having a bulk density of 0.23 g/cm$^3$ or less, sugar alcohol and pregelatinized starch—other ingredients may be incorporated where necessary.

The process for producing the orally disintegrating tablet of embodiment B comprises the steps of: Producing the drug-containing granules where desired, and mixing the drug or drug-containing granules and other ingredients and compressing the mixture.

The step of producing the drug-containing granules is similar to the above-mentioned A-2.

In the step of mixing the drug or drug-containing granules and other ingredients and compressing the mixture, the step of mixing or compression is similar to the above-mentioned A-3.

Embodiment C

An orally disintegrating tablet obtainable by compressing drug-containing granules comprising a powdery drug, a crystalline cellulose having a bulk density of 0.23 g/cm$^3$ or less, a sugar alcohol and a pregelatinized starch In this embodiment, the drug-containing granules impart desirable disintegration properties and moldability to an orally disintegrating tablet. Where necessary, ingredients such as a commonly-used disintegrating agent may be incorporated in the granules or outside of the granules.

The process for producing the orally disintegrating tablet of embodiment C comprises the steps of producing the drug-containing granules and mixing with other ingredients where desired, and compressing the mixture.

The step of producing the drug-containing granules is similar to the above-mentioned A-1, except that the drug is added to the mixture. The step of compression is similar to that in the above-mentioned A-3.

The thus-obtained orally disintegrating tablets of the present invention is excellent in terms of disintegration properties and solubility when they are placed in the oral cavity or put into water, and are also excellent in terms of physical and chemical stabilities.

The disintegration properties or solubility of the orally disintegrating tablet of the present invention are such that the time required for disintegration and dissolution in the oral cavity (the time required for complete solution of the tablet in only saliva without including water in the mouth, in the oral cavity of a healthy adult male) is generally about 5 to 120 seconds, preferably about 5 to 60 seconds, further preferably about 5 to 40 seconds.

The orally disintegrating tablet of the present invention gradually disintegrates or dissolves by saliva when the tablet is placed in the mouth, and disintegrates or dissolves in a shorter time in the case of compression in the oral cavity, i.e., pressure by the upper jaw and tongue, or friction by the tongue, i.e., an action of "licking", or the like. In a person whose oral cavity is dry or a person whose amount of saliva is small, the tablet may be disintegrated or dissolved in the oral cavity using water or hot water, or the tablet can be taken as it is together with water as in conventional tablets.

On the other hand, the orally disintegrating tablet of the present invention has a hardness by which the tablet does not disintegrate in the production steps or distribution process, even after a stability test under temperature and humidity (for example, a temperature of 25° C., a humidity of 75%, an open system, 1 week).

Therefore, the tablet has a hardness by which the tablet does not disintegrate in the production steps or distribution process of a formulation, has a viable hardness even in storage under temperature and humidity, and also has excellent storage stability.

The orally disintegrating tablet of the present invention can be used for the treatment, prevention or diagnosis of various diseases as a formulation that is also easily taken by the elderly, children or aphagia patients, or as a safe formulation for general adult humans.

EXAMPLES

The following Examples are provided for the purpose of illustration, and are not to be construed as limiting the present invention to these Examples. Furthermore, since the pharmaceutical properties of the orally disintegrating tablet are not significantly affected by the drug added, the experiments were conducted without adding a drug in many of the Examples.

Comparative Example 1

910 g of D-mannitol (manufactured by Merck) was put into a fluidized bed granulator (manufactured by Freund, Type FLO-2), and a liquid in which 35 g of a pregelatinized starch (manufactured by Asahi Kasei Chemicals Corporation, swelstar PD-1) was dispersed in 600 g of purified water was sprayed thereon and dried to give a granulated product. 495 g of the obtained granulated product was mixed with 5 g of magnesium stearate (manufactured by Mallinckrodt, Inc.), and the mixture was tabletted in a rotary tabletting machine at tabletting pressures of 8 kN and 10 kN to give an orally disintegrating tablet (tablet diameter: 9 mmφ, mass: 280 mg).

Comparative Example 2

3,600 g of D-mannitol (manufactured by Merck) and 1,600 g of a crystalline cellulose (manufactured by Asahi Kasei Chemicals Corporation, CEOLUS PH302, bulk density: 0.35-0.46 g/cm$^3$) were put into a fluidized bed granulator (manufactured by Freund, Type FLO-5), and a liquid in which 200 g of a pregelatinized starch (manufactured by Asahi Kasei Chemicals Corporation, swelstar PD-1) was dispersed in 1,800 g of purified water was sprayed thereon and dried to give a granulated product. 495 g of the obtained granulated product was mixed with 5 g of magnesium stearate (manufactured by Mallinckrodt, Inc.), and the mixture was tabletted in a rotary tabletting machine at a tabletting pressure of 10 kN to give an orally disintegrating tablet (tablet diameter: 9 mmφ, mass: 280 mg).

Example 1

4,360 g of D-mannitol (manufactured by Merck) and 520 g of a crystalline cellulose (manufactured by Asahi Kasei Chemicals Corporation, CEOLUS KG-1000, bulk density: 0.10-0.15 g/cm$^3$) were put into a fluidized bed granulator (manufactured by Freund, Type FLO-5), a liquid in which 200 g of a pregelatinized starch (manufactured by Asahi Kasei Chemicals Corporation, swelstar PD-1) was dispersed in 2,300 g of purified water was sprayed thereon, and drying was then conducted to give a granulated product.

495 g of the obtained granulated product was mixed with 5 g of magnesium stearate (manufactured by Mallinckrodt, Inc.), and the mixture was tabletted in a rotary tabletting machine at a tabletting pressure of 12 kN to give an orally disintegrating tablet (tablet diameter: 9 mmφ, mass: 280 mg).

Example 2

3,880 g of D-mannitol (manufactured by Merck) and 1,000 g of a crystalline cellulose (manufactured by Asahi Kasei Chemicals Corporation, CEOLUS KG-1000, bulk density: 0.10-0.15 g/cm$^3$) were put into a fluidized bed granulator (manufactured by Freund, Type FLO-5), a liquid in which 200 g of a pregelatinized starch (manufactured by Asahi Kasei Chemicals Corporation, swelstar PD-1) was dispersed in 2,300 g of purified water was sprayed thereon, and drying was then conducted to give a granulated product.

495 g of the obtained granulated product was mixed with 5 g of magnesium stearate (manufactured by Mallinckrodt, Inc.), and the mixture was tabletted in a rotary tabletting machine at a tabletting pressure of 12 kN to give an orally disintegrating tablet (tablet diameter: 9 mmφ, mass: 280 mg).

Example 3

9,240 g of D-mannitol (manufactured by Merck) and 4,180 g of a crystalline cellulose (manufactured by Asahi Kasei Chemicals Corporation, CEOLUS KG-1000, bulk density: 0.10-0.15 g/cm$^3$) were put into a fluidized bed granulator (manufactured by Powrex Corporation, GPCG-15), a liquid in which 550 g of a pregelatinized starch (manufactured by Asahi Kasei Chemicals Corporation, swelstar PD-1) was dispersed in 6,325 g of purified water was sprayed thereon, and drying was then conducted to give a granulated product.

495 g of the obtained granulated product was mixed with 5 g of magnesium stearate (manufactured by Mallinckrodt, Inc.), and the mixture was tabletted in a rotary tabletting machine at a tabletting pressure of 10 kN to give an orally disintegrating tablet (tablet diameter: 9 mmφ, mass: 280 mg).

Example 4

2,880 g of D-mannitol (manufactured by Merck) and 2,000 g of a crystalline cellulose (manufactured by Asahi Kasei Chemicals Corporation, CEOLUS KG-1000, bulk density: 0.10-0.15 g/cm$^3$) were put into a fluidized bed granulator (manufactured by Freund, Type FLO-5), a liquid in which 200 g of a pregelatinized starch (manufactured by Asahi Kasei Chemicals Corporation, swelstar PD-1) was dispersed in 2,300 g of purified water was sprayed thereon, and drying was then conducted to give a granulated product.

495 g of the obtained granulated product was mixed with 5 g of magnesium stearate (manufactured by Mallinckrodt, Inc.), and the mixture was tabletted in a rotary tabletting machine at a tabletting pressure of 6 kN to give an orally disintegrating tablet (tablet diameter: 9 mmφ, mass: 280 mg).

Example 5

3,360 g of D-mannitol (manufactured by Merck) and 1520 g of a crystalline cellulose (manufactured by Asahi Kasei Chemicals Corporation, CEOLUS KG-802, bulk density: 0.13-0.23 g/cm$^3$) were put into a fluidized bed granulator (manufactured by Freund, Type FLO-5), a liquid in which 200 g of a pregelatinized starch (manufactured by Asahi Kasei Chemicals Corporation, swelstar PD-1) was dispersed in 2,300 g of purified water was sprayed thereon, and drying was then conducted to give a granulated product.

495 g of the obtained granulated product was mixed with 5 g of magnesium stearate (manufactured by Mallinckrodt, Inc.), and the mixture was tabletted in a rotary tabletting machine at a tabletting pressure of 10 kN to give an orally disintegrating tablet (tablet diameter: 9 mmφ, mass: 280 mg).

Example 6

672 g of D-mannitol (manufactured by Merck), 304 g of a crystalline cellulose (manufactured by Asahi Kasei Chemicals Corporation, CEOLUS KG-1000, bulk density: 0.10-0.15 g/cm$^3$) and 40 g of a pregelatinized starch (manufactured by Asahi Kasei Chemicals Corporation, swelstar PD-1) were mixed to give a mixture.

495 g of the obtained mixture was mixed with 5 g of magnesium stearate (manufactured by Mallinckrodt, Inc.), and the mixture was tabletted in a rotary tabletting machine at a tabletting pressure of 10 kN to give an orally disintegrating tablet (tablet diameter: 9 mmφ, mass: 280 mg).

Example 7

840 g of D-mannitol (manufactured by Merck), 380 g of a crystalline cellulose (manufactured by Asahi Kasei Chemicals Corporation, CEOLUS KG-1000, bulk density: 0.10-0.15 g/cm$^3$) and 50 g of a pregelatinized starch (manufactured by Asahi Kasei Chemicals Corporation, swelstar PD-1) were put into a fluidized bed granulator (manufactured by Freund, Type FLO-2), 575 g of purified water was sprayed, and drying was then conducted to give a granulated product.

495 g of the obtained granulated product was mixed with 5 g of magnesium stearate (manufactured by Mallinckrodt, Inc.), and the mixture was tabletted in a rotary tabletting machine at a tabletting pressure of 12 kN to give an orally disintegrating tablet (tablet diameter: 9 mmφ, mass: 280 mg).

Example 8

252 g of D-mannitol (manufactured by Merck) and 114 g of a crystalline cellulose (manufactured by Asahi Kasei Chemicals Corporation, CEOLUS KG-1000, bulk density: 0.10-0.15 g/cm$^3$) were put into a high-shear granulator (manufactured by Powrex Corporation, Type VG-5) and kneaded while a liquid in which 15 g of a pregelatinized starch (manufactured by Asahi Kasei Chemicals Corporation, swelstar PD-1) was dispersed in 135 g of purified water was added dropwise thereto. The kneaded product was put into a fluidized bed granulator (manufactured by Freund, Type FLO-2) and dried to give a granulated product.

198 g of the obtained granulated product was mixed with 2 g of magnesium stearate (manufactured by Mallinckrodt, Inc.), and the mixture was tabletted in a rotary tabletting machine at a tabletting pressure of 6 kN to give an orally disintegrating tablet (tablet diameter: 9 mmφ, mass: 280 mg).

Example 9

480 g of a granulated product that had been obtained by the same process as that in the former stage of Example 3 and 15 g of crospovidone (manufactured by BASF, KOLLIDON CL-F) were mixed to give a mixture. 495 g of the obtained mixture was mixed with 5 g of magnesium stearate (manufactured by Mallinckrodt, Inc.), and the mixture was tabletted in a rotary tabletting machine at a tabletting pressure of 10 kN to give an orally disintegrating tablet (tablet diameter: 9 mmφ, mass: 280 mg).

Example 10

465 g of a granulated product that had been obtained by the same process as that in the former stage of Example 3 and 30 g of crospovidone (manufactured by BASF, KOLLIDON CL-F) were mixed to give a mixture. 495 g of the obtained mixture was mixed with 5 g of magnesium stearate (manufactured by Mallinckrodt, Inc.), and the mixture was tabletted in a rotary tabletting machine at a tabletting pressure of 10 kN to give an orally disintegrating tablet (tablet diameter: 9 mmφ, mass: 280 mg).

Example 11

455 g of a granulated product that had been obtained by the same process as that in the former stage of Example 3 and 40 g of carmellose calcium (manufactured by Gotoku Chemical Co., Ltd., ECG-505) were mixed to give a mixture. 495 g of the obtained mixture was mixed with 5 g of magnesium stearate (manufactured by Mallinckrodt, Inc.), and the mixture was tabletted in a rotary tabletting machine at a tabletting pressure of 8 kN to give an orally disintegrating tablet (tablet diameter: 9 mmφ, mass: 280 mg).

Example 12

2,590 g of D-mannitol (manufactured by Merck), 1,610 g of a crystalline cellulose (manufactured by Asahi Kasei Chemicals Corporation, CEOLUS KG-1000, bulk density: 0.10-0.15 g/cm$^3$) and 385 g of carmellose calcium (manufactured by Gotoku Chemical Co., Ltd., ECG-505) were put into a fluidized bed granulator (manufactured by Freund, Type FLO-5), a liquid in which 175 g of a pregelatinized starch (manufactured by Asahi Kasei Chemicals Corporation, swelstar PD-1) was dispersed in 3,000 g of purified water was sprayed thereon, and drying was then conducted to give a granulated product. 495 g of the obtained granulated product was mixed with 5 g of magnesium stearate (manufactured by Mallinckrodt, Inc.), and the mixture was tabletted in a rotary tabletting machine at a tabletting pressure of 6 kN to give an orally disintegrating tablet (tablet diameter: 9 mmφ, mass: 280 mg).

Example 13

266 g of D-mannitol (manufactured by Merck), 266 g of D-mannitol (manufactured by Merck, PARTECK M100), 329 g of a crystalline cellulose (manufactured by Asahi Kasei Chemicals Corporation, CEOLUS KG-1000, bulk density: 0.10-0.15 g/cm$^3$) and 56 g of crospovidone (manufactured by BASF, KOLLIDON CL-F) were put into a fluidized bed granulator (manufactured by Freund, Type FLO-2), a liquid in which 35 g of a pregelatinized starch (manufactured by Asahi Kasei Chemicals Corporation, swelstar PD-1) was dispersed in 600 g of purified water was sprayed thereon, and drying was then conducted to give a granulated product. 495 g of the obtained granulated product was mixed with 5 g of magnesium stearate (manufactured by Mallinckrodt, Inc.), and the mixture was tabletted in a rotary tabletting machine at a tabletting pressure of 8 kN to give an orally disintegrating tablet (tablet diameter: 9 mmφ, mass: 280 mg).

Example 14

40 g of memantine hydrochloride, 460 g of a granulated product that had been obtained by the same process as that in the former stage of Example 3, 33.84 g of crospovidone (manufactured by BASF, KOLLIDON CL-F), 20 g of Aspartame (manufactured by Ajinomoto) and 0.56 g of a flavor material (manufactured by Takasago International Corporation) were mixed to give a mixture. 554.4 g of the obtained mixture was mixed with 5.6 g of magnesium stearate (manufactured by Mallinckrodt, Inc.), and the mixture was tabletted in a rotary tabletting machine at a tabletting pressure of 12 kN to give an orally disintegrating tablet (tablet diameter: 9=0, mass: 280 mg).

Example 15

3,000 g of memantine hydrochloride, 6,000 g of D-mannitol (manufactured by Merck), 1,200 g of a crystalline cellulose (manufactured by Asahi Kasei Chemicals Corporation, CEOLUS PH101) and 675 g of carmellose calcium (manufactured by Gotoku Chemical Co., Ltd., ECG-505) were put into a fluidized bed granulator (manufactured by Powrex Corporation, GPCG-15), a liquid in which 375 g of hydroxypropyl cellulose (manufactured by Nippon Soda Co., Ltd., HPC-L) was dissolved in 5,875 g of purified water was sprayed thereon, and drying was then conducted to give a drug-containing granulated product.

150 g of the drug-containing granulated product, 350 g of a granulated product that had been obtained by the same process as that in the former stage of Example 3, 33.84 g of crospovidone (manufactured by BASF, KOLLIDON CL-F), 20 g of Aspartame (manufactured by Ajinomoto Co., Inc.) and 0.56 g of a flavor material (manufactured by Takasago International Corporation) were mixed to give a mixture. 554.4 g of the obtained mixture was mixed with 5.6 g of magnesium stearate (manufactured by Mallinckrodt, Inc.), and the mixture was tabletted in a rotary tabletting machine at a tabletting pressure of 12 kN to give an orally disintegrating tablet (tablet diameter: 9 mmφ, mass: 280 mg).

Example 16

10,500 g of a drug-containing granulated product that had been obtained by the same process as that in the former stage of Example 15 was put into a fluidized bed granulator (manufactured by Powrex Corporation, GPCG-15), 27,020 g of a coating liquid (composition: 51.8% of methacrylic acid copolymer LD (manufactured by Evonik Industries, EUDRAGIT L30D-55), 1.6% of triethyl citrate (manufactured by Morimura Bros., Inc., CITROFLEX), 7.8% of talc (manufactured by Matsumura Sangyo) and 38.8% of purified water) was sprayed thereon, and drying was then conducted to give a drug-containing coating product.

3,690 g of the drug-containing coating product, 3,810 g of a granulated product that had been obtained by the same process as that in the former stage of Example 3, 507.6 g of crospovidone (manufactured by BASF, KOLLIDON CL-F), 300 g of Aspartame (manufactured by Ajinomoto Co., Inc.) and 8.4 g of a flavor material (manufactured by Takasago International Corporation) were mixed to give a mixture. 8,316 g of the obtained mixture was mixed with 84 g of magnesium stearate (manufactured by Mallinckrodt, Inc.), and the mixture was tabletted in a rotary tabletting machine at a tabletting pressure of 10 kN to give an orally disintegrating tablet (tablet diameter: 9 mmφ, mass: 280 mg).

Example 17

4.89 g of a drug-containing coating product that had been obtained by the same process as that in the former stage of Example 16, 2.91 g of a granulated product that had been obtained by the same process as that in the former stage of Example 3, and 0.52 g of crospovidone (manufactured by BASF, KOLLIDON CL-F) were mixed to give a mixture. 8.32 g of the obtained mixture was mixed with 0.084 g of magnesium stearate (manufactured by Mallinckrodt, Inc.), and the mixture was tabletted in a single punch tabletting machine at a tabletting pressure of 10 kN to give an orally disintegrating tablet (tablet diameter: 9 mmφ, mass: 280 mg)

Example 18

42.38 g of hydromorphone hydrochloride, 2,677.5 g of a granulated product that had been obtained by the same process as that in the former stage of Example 3 and 250.1 g of low-substituted hydroxypropyl cellulose (manufactured by Shin-Etsu Chemical Co., Ltd., L-HPC (LH-11)) were mixed to give a mixture. 2,970 g of the obtained mixture was mixed with 30 g of magnesium stearate (manufactured by Mallinckrodt, Inc.) to give a mixture for tabletting. The mixture for tabletting was tabletted in a rotary tabletting machine at a tabletting pressure of 6 kN to give an orally disintegrating tablet (tablet diameter: 6 mmφ, mass: 80 mg).

Example 19

The mixture for tabletting obtained in Example 18 was tabletted in a rotary tabletting machine at a tabletting pressure of 10 kN to give an orally disintegrating tablet (tablet diameter: 9.5 mmφ, mass: 320 mg).

Test Example

The tablets obtained in the Examples and Comparative Examples were evaluated according to the following methods.

The hardness was measured by a tablet continuous measurement device (WHT: manufactured by Pharm Test) (the average value of ten tablets is described).

The oral disintegration time was obtained by measuring the time required for complete disintegration of a test tablet under the state in which the tablet was placed in the oral cavity of a healthy adult male without being bitten (the average value of six samples is described). For the tablets obtained in Examples 18 and 19, the disintegration time was measured according to the "Disintegration Test" in the 16th Revised Japanese Pharmacopoeia, instead of the oral disintegration time (the average value of three samples is described).

The friability was measured according to the "Tablet Friability Test" in the 16th Revised Japanese Pharmacopoeia (10 tablets).

The results are shown in Table 1 to Table 5.

TABLE 1

|  | Comparative Example 1 | Comparative Example 2 |
| --- | --- | --- |
| Tabletting pressure [kN] | 8 | 10 | 10 |
| Hardness [kg] | 3.3 | 3.6 | 5.3 |
| Oral disintegration time [s] | 30 | 38 | 29 |
| Friability [%] | 6.2 | 3.7 | 1.8 |
| Number of cracked tablet(s) after friability test (among 10 tablets) | 7 | 3 | 2 |

TABLE 2

|  | Example 1 | Example 2 | Example 3 | Example 4 | Example 5 | Example 6 |
| --- | --- | --- | --- | --- | --- | --- |
| Tabletting pressure [kN] | 12 | 12 | 10 | 6 | 10 | 10 |
| Hardness [kg] | 6.0 | 7.4 | 10.4 | 8.1 | 7.1 | 8.3 |
| Oral disintegration time [s] | 32 | 33 | 33 | 23 | 29 | 24 |
| Friability [%] | 0.8 | 0.4 | 0.0 | 0.1 | 0.3 | 0.1 |
| Number of cracked tablet(s) after friability test (among 10 tablets) | 0 | 0 | 0 | 0 | 0 | 0 |

TABLE 3

|  | Example 7 | Example 8 | Example 9 | Example 10 | Example 11 | Example 12 |
|---|---|---|---|---|---|---|
| Tabletting pressure [kN] | 12 | 6 | 10 | 10 | 8 | 6 |
| Hardness [kg] | 7.6 | 6.5 | 10.8 | 8.7 | 7.6 | 7.3 |
| Oral disintegration time [s] | 26 | 26 | 18 | 16 | 34 | 27 |
| Friability [%] | 0.3 | 0.2 | 0.0 | 0.0 | 0.2 | 0.2 |
| Number of cracked tablet(s) after friability test (among 10 tablets) | 0 | 0 | 0 | 0 | 0 | 0 |

TABLE 4

|  | Example 13 | Example 14 | Example 15 | Example 16 | Example 17 |
|---|---|---|---|---|---|
| Tabletting pressure [kN] | 8 | 12 | 12 | 10 | 10 |
| Hardness [kg] | 12.6 | 8.8 | 8.8 | 8.8 | 7.0 |
| Oral disintegration time [s] | 27 | 18 | 32 | 36 | 22 |
| Friability [%] | 0.0 | 0.0 | 0.0 | 0.0 | 0.0 |
| Number of cracked tablet(s) after friability test (among 10 tablets) | 0 | 0 | 0 | 0 | 0 |

TABLE 5

|  | Example 18 | Example 19 |
|---|---|---|
| Tabletting pressure [kN] | 6 | 10 |
| Hardness [kg] | 3.3 | 7.0 |
| Disintegration time [s] | 31 | 28 |
| Friability [%] | 0.2 | 0.3 |
| Number of cracked tablet(s) after friability test (among 10 tablets) | 0 | 0 |

In the case where a crystalline cellulose is not incorporated as in Comparative Example 1, the oral disintegrating time is fast but the friability is high, at 1% or more, and cracked tablets are generated after the friability test, and thus it is difficult to produce an orally disintegrating tablet having well-balanced hardness and disintegration properties. Furthermore, even in the case where D-mannitol and a crystalline cellulose having a high bulk density are incorporated as in Comparative Example 2, the friability and hardness are slightly improved but the friability is high and cracked tablets are generated, and the oral disintegrating time is extended, and thus it is difficult to produce an orally disintegrating tablet having well-balanced hardness and disintegration properties.

On the other hand, it was found that, when D-mannitol and a crystalline cellulose having a bulk density of 0.23 g/cm$^3$ or less are incorporated as in Examples 1 to 19, it becomes possible to produce a favorable orally disintegrating tablet that ensures the property of quick oral disintegration and has high hardness and small friability, and does not generate cracked tablets.

Furthermore, it was proved that the technique of granulation by spraying or adding a liquid in which a pregelatinized starch is dispersed in purified water is a very useful technique for the production of an orally disintegrating tablet, since the technique provides improvement in flowability and compressibility

INDUSTRIAL APPLICABILITY

Since the orally disintegrating tablet of the present invention has the property of quick disintegration and solubility when it is put into the oral cavity or water, it may easily be taken, has a sufficient hardness in the production steps and distribution steps, and has excellent storage stability. Therefore, it can be widely used for therapeutic drugs and diagnostic drugs for the elderly, children or aphagia patients. Furthermore, the orally disintegrating tablet of the present invention can be produced by conventional compression without requiring special equipment, and is also excellent in terms of industrial production.

The invention claimed is:
1. An orally disintegrating tablet comprising:
a drug;
a crystalline cellulose having a bulk density of 0.23 g/cm$^3$ or less;
a sugar alcohol; and
a pregelatinized starch;
wherein the orally disintegrating tablet is obtained by compressing drug-free granules comprising a crystalline cellulose having a bulk density of 0.23 g/cm$^3$ or less, a sugar alcohol and a pregelatinized starch, and a drug or drug-containing granules.
2. The orally disintegrating tablet according to claim 1, wherein the crystalline cellulose has a bulk density of from 0.10 g/cm$^3$ to 0.23 g/cm$^3$.
3. The orally disintegrating tablet according to claim 1, wherein the crystalline cellulose has a bulk density of 0.15 g/cm$^3$ or less.
4. The orally disintegrating tablet according to claim 1, wherein the incorporation amount of the crystalline cellulose in the disintegrating tablet is 5 to 50% by weight.
5. The orally disintegrating tablet according to claim 1, wherein the pregelatinized starch has an average degree of gelatinization of 90% or less.
6. The orally disintegrating tablet according to claim 1, wherein the sugar alcohol is D-mannitol.
7. The orally disintegrating tablet according to claim 1, further comprising a disintegrating agent.

8. The orally disintegrating tablet according to claim 7, wherein the disintegrating agent is one kind or two or more kinds selected from the group consisting of crospovidone, carmellose calcium, carmellose, croscarmellose sodium, low-substituted hydroxypropyl cellulose, corn starch and sodium starch glycolate.

9. The orally disintegrating tablet according to claim 1, further comprising a lubricant.

10. The orally disintegrating tablet according to claim 9, wherein the lubricant is one kind or two or more kinds selected from the group consisting of magnesium stearate, calcium stearate, sodium stearyl fumarate and talc.

11. The orally disintegrating tablet according to claim 1, wherein the drug is memantine or a pharmaceutically acceptable salt thereof.

12. The orally disintegrating tablet according to claim 11, wherein the pharmaceutically acceptable salt of memantine is memantine hydrochloride.

13. A process for the production of an orally disintegrating tablet, comprising:
mixing and compressing drug-free granules, a powdery or granulated drug, and an additive where desired, wherein the drug-free granules are obtainable by wet-granulating a mixture containing a crystalline cellulose having a bulk density of 0.23 g/cm$^3$ or less and a sugar alcohol with a liquid in which a pregelatinized starch is dissolved or dispersed, or by wet-granulating a mixture comprising the crystalline cellulose having a bulk density of 0.23 g/cm$^3$ or less, sugar alcohol and pregelatinized starch with water and drying the product.

14. The process for the production of an orally disintegrating tablet according to claim 13, wherein the wet-granulating is fluidized bed granulating.

15. The process for the production of an orally disintegrating tablet according to claim 13, wherein a disintegrating agent is further included in the mixture or other additive.

16. The process for the production of an orally disintegrating tablet according to claim 13, which comprises adding a lubricant before conducting the compression.

17. The process for the production of an orally disintegrating tablet according to claim 13, wherein the powdery or granulated drug comprises a coating provided on the surface of the drug.

18. The process for the production of an orally disintegrating tablet according to claim 13, wherein the drug is memantine or a pharmaceutically acceptable salt thereof.

19. The process for the production of an orally disintegrating tablet according to claim 18, wherein the memantine or a pharmaceutically acceptable salt is memantine hydrochloride.

20. A process for the production of a tablet, comprising compressing a drug or drug-containing granules with drug-free granules comprising a crystalline cellulose having a bulk density of 0.23 g/cm$^3$ or less, a sugar alcohol and a pregelatinized starch.

21. The process according to claim 20, further comprising granulating a mixed powder comprising a crystalline cellulose having a bulk density of 0.23 g/cm$^3$ or less and a sugar alcohol with a liquid in which a pregelatinized starch is dissolved or dispersed, to provide the drug-free granules.

22. The process according to claim 20, wherein the drug-containing granules or drug-free granules further comprises a disintegrating agent.

23. The process according to claim 22, wherein the disintegrating agent is one kind or two or more kinds selected from the group consisting of crospovidone, carmellose calcium, carmellose, croscarmellose sodium, low-substituted hydroxypropyl cellulose, corn starch and sodium starch glycolate.

24. The process according to claim 20, wherein the drug is memantine or a pharmaceutically acceptable salt thereof.

* * * * *